(12) United States Patent
Salmon et al.

(10) Patent No.: US 7,271,130 B2
(45) Date of Patent: Sep. 18, 2007

(54) N-ALKYNYL-2-(SUBSTITUTED PHENOXY) ALKYLAMIDES AND THEIR USE AS FUNGICIDES

(75) Inventors: Roger Salmon, Bracknell (GB); David William Langton, Bracknell (GB)

(73) Assignee: Syngenta Limited (GB)

( * ) Notice: Subject to any disclaimer, the term of this patent is extended or adjusted under 35 U.S.C. 154(b) by 65 days.

(21) Appl. No.: 10/536,517

(22) PCT Filed: Nov. 10, 2003

(86) PCT No.: PCT/GB03/04834

§ 371 (c)(1), (2), (4) Date: Mar. 6, 2006

(87) PCT Pub. No.: WO2004/048316

PCT Pub. Date: Jun. 10, 2004

(65) Prior Publication Data

US 2006/0194763 A1     Aug. 31, 2006

(30) Foreign Application Priority Data

Nov. 26, 2002  (GB) ................. 0227556.8

(51) Int. Cl.
  *A01N 43/00* (2006.01)
  *A01N 43/02* (2006.01)
  *A01N 33/00* (2006.01)
  *C07D 205/00* (2006.01)
  *C07D 203/04* (2006.01)

(52) U.S. Cl. ............... 504/209; 504/288; 504/291; 504/326; 548/950; 548/954; 549/88; 549/90; 549/200; 564/123

(58) Field of Classification Search ......... 514/622; 504/209, 288, 291, 326; 548/950, 954; 549/88, 549/90, 200; 564/123
See application file for complete search history.

(56) References Cited

U.S. PATENT DOCUMENTS

| 3,272,844 A | 9/1966 | Easton et al. |
| 4,049,423 A | 9/1977 | Baker et al. |
| 4,062,977 A | 12/1977 | Baker et al. |
| 4,070,486 A | 1/1978 | Baker et al. |
| 4,083,867 A | 4/1978 | Baker et al. |
| 4,116,677 A | 9/1978 | Walker et al. |
| 4,146,387 A | 3/1979 | Thiele |
| 4,154,849 A | 5/1979 | Walker et al. |
| 4,168,319 A | 9/1979 | Walker et al. |
| 4,784,682 A | 11/1988 | Forster et al. |
| 6,048,860 A | 4/2000 | Farrar et al. |
| 6,090,815 A | 7/2000 | Masuda et al. |
| 6,156,769 A | 12/2000 | Farrar et al. |
| 2005/0065032 A1 | 3/2005 | Whittingham et al. |
| 2006/0019973 A1 | 1/2006 | Salmon et al. |
| 2006/0058397 A1 | 3/2006 | Salmon |
| 2006/0140997 A1 | 6/2006 | Pitterna et al. |
| 2006/0148859 A1 | 7/2006 | Crowley |

FOREIGN PATENT DOCUMENTS

| CA | 1132580 A | 9/1982 |
| DE | 2731960 A1 | 2/1978 |
| DE | 2948095 | 6/1981 |
| DE | 3702964 | 8/1988 |
| EP | 0001721 | 5/1979 |
| EP | 0010298 | 4/1980 |
| EP | 0751120 | 1/1997 |
| EP | 0940392 A1 | 9/1999 |
| FR | 2359816 | 2/1978 |
| JP | 04021677 | 1/1992 |
| JP | 2001089453 A | 4/2001 |
| WO | 06186702 A | 7/1994 |
| WO | 9933810 A1 | 7/1999 |
| WO | 03048128 A1 | 6/2003 |
| WO | 0452100 A1 | 6/2004 |
| WO | 04047538 A1 | 6/2004 |
| WO | 04048316 A1 | 6/2004 |
| WO | 04048337 A1 | 6/2004 |
| WO | 04108663 A1 | 12/2004 |
| WO | 04108694 A1 | 12/2004 |
| WO | 06058699 A1 | 6/2006 |
| WO | 06058700 A1 | 6/2006 |

*Primary Examiner*—Alton Pryor
(74) *Attorney, Agent, or Firm*—Jacqueline Haley

(57) ABSTRACT

Fungicidal compounds of the general formula (1) wherein X, Y, Z, $R_1$, $R_2$, $R_3$, $R_4$ and $R_5$ have the definitions given in claim 1

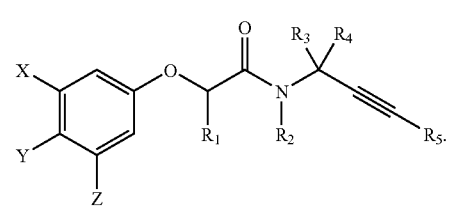

(1)

11 Claims, No Drawings

N-ALKYNYL-2-(SUBSTITUTED PHENOXY) ALKYLAMIDES AND THEIR USE AS FUNGICIDES

This application is a 371 of International Application No. PCT/GB2003/004834 filed Nov. 10, 2003, which claims priority to GB 0227556.8, filed Nov. 26, 2002, the contents of which are incorporated herein by reference.

This invention relates to novel N-alkynyl-2-(substituted phenoxy)alkylamides, to processes for preparing them, to compositions containing them and to methods of using them to combat fungi, especially fungal infections of plants.

Certain N-alkynyl-2-(substituted phenoxy)alkylamides are described in U.S. Pat. No. 4,083,867 and U.S. Pat. No. 4,116,677 as being useful as herbicides. Others are described in U.S. Pat. No. 4,168,319 as being useful as mildewicides.

The present invention is concerned with the provision of particular N-alkynyl-2-(substituted phenoxy)alkylamides for use as plant fungicides.

Thus according to the present invention there is provided a compound of the general formula (1):

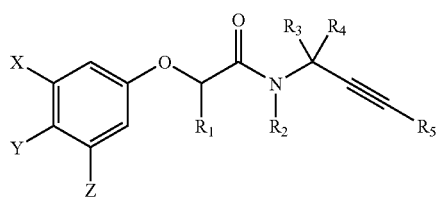

(1)

wherein

X, Y and Z are independently H, halogen, $C_{1-4}$ alkyl (e.g. methyl), halo($C_{1-4}$)alkyl (e.g. trifluoromethyl), $C_{2-4}$ alkenyl, halo($C_{2-4}$)alkenyl, $C_{2-4}$ alkynyl, halo($C_{2-4}$)alkynyl, $C_{1-4}$ alkoxy (e.g. methoxy), halo($C_{1-4}$)alkoxy (e.g. trifluoromethoxy), —S(O)$_n$($C_{1-4}$)alkyl where n is 0, 1 or 2 and the alkyl group is optionally substituted with fluoro (e.g. methylthio, tri-fluoromethylsulphonyl), —OSO$_2$($C_{1-4}$)alkyl where the alkyl group is optionally substituted with fluoro (e.g. trifluoromethylsulphonyloxy), cyano, nitro, $C_{1-4}$ alkoxycarbonyl, —CONR'R", —COR', —NR'COR" or —NR'COOR''' where R' and R" are independently H or $C_{1-4}$ alkyl and R''' is $C_{1-4}$ alkyl (e.g. acetyl, —NHCOCH$_3$ and —NHCO$_2$CH$_3$), provided that at least one of X and Z is other than H;

R$_1$ is alkoxyalkyl, alkylthioalkyl, alkylsulphinylalkyl or alkylsulphonylalkyl in which the total number of carbon atoms is 2 or 3 (e.g. methoxymethyl, methylthiomethyl, ethoxymethyl, 2-methoxyethyl and 2-methylthioethyl);

R$_2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy; R$_3$ and R$_4$ are independently H, $C_{1-3}$ alkyl, $C_{2-3}$ alkenyl or $C_{2-3}$ alkynyl provided that both are not H and that when both are other than H their combined total of carbon atoms does not exceed 4, or R$_3$ and R$_4$ join with the carbon atom to which they are attached to form a 3 or 4 membered carbocyclic ring optionally containing one O, S or N atom and optionally substituted with halo or $C_{1-4}$ alkyl; and R$_5$ is H, $C_{1-4}$ alkyl or $C_{3-6}$ cycloalkyl in which the alkyl or cycloalkyl group is optionally substituted with halo, hydroxy, $C_{1-6}$ alkoxy, cyano, $C_{1-4}$ alkylcarbonyloxy, amino-carbonyloxy, mono- or di($C_{1-4}$)alkylaminocarbonyloxy, —S(O)$_n$($C_{1-6}$)alkyl where n is 0, 1 to or 2, triazolyl (e.g. 1,2,4-triazol-1-yl), tri($C_{1-4}$)alkylsilyloxy, optionally substituted phenoxy, optionally substituted thienyloxy, optionally substituted benzyloxy or optionally substituted thienylmethoxy, or R$_5$ is optionally substituted phenyl, optionally substituted thienyl or optionally substituted benzyl, in which the optionally substituted phenyl and thienyl rings of the R$_5$ values are optionally substituted with one, two or three substituents selected from halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl; $C_{3-6}$ cycloalkyl($C_{1-4}$)alkyl, phenoxy, benzyloxy, benzoyloxy, cyano, isocyano, thiocyanato, isothiocyanato, nitro, —NR'''R", —NHCOR''', —NHCONR'''R", —CONR'''R", —SO$_2$R''', —OSO$_2$R''', —COR''', —CR'''=NR" or —N=CR'''R", in which R''' and R" are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

The compounds of the invention contain at least one asymmetric carbon atom (and at least two when R$_3$ and R$_4$ are different) and may exist as enantiomers (or as pairs of diastereoisomers) or as mixtures of such. However, these mixtures may be separated into individual isomers or isomer pairs, and this invention embraces such isomers and mixtures thereof in all proportions. It is to be expected that for any given compound, one isomer may be more fungicidally active than another.

Except where otherwise stated, alkyl groups and alkyl moieties of alkoxy, alkylthio, etc., suitably contain from 1 to 4 carbon atoms in the form of straight or branched chains. Examples are methyl, ethyl, n-and iso-propyl and n-, sec-, iso- and tert-butyl. Where alkyl moieties contain 5 or 6 carbon atoms, examples are n-pentyl and n-hexyl.

Alkenyl and alkynyl moieties also suitable contain from 2 to 4 carbon atoms in the form of straight or branched chains. Examples are allyl, ethynyl and propargyl.

Halo includes fluoro, chloro, bromo and iodo. Most commonly it is fluoro, chloro or bromo and usually fluoro or chloro.

The substituents X, Y and Z on the phenyl ring of formula (1) may provide a 3-, 3,5- or 3,4,5-substituted phenyl ring. Typically X, Y and Z are all chloro or methyl, or X and Z are both chloro or bromo and Y is H or methyl, or X and Z are both methyl or methoxy and Y is H, chloro, bromo or alkylthio, or X is methoxy, Y is H and Z is cyano or chloro, or X is methyl, Y is H and Z is ethyl, or X is chloro, bromo or trifluoromethyl and both Y and Z are H.

Typically, R$_1$ is methoxymethyl, methylthiomethyl, ethoxymethyl, 2-methoxy-ethyl and 2-methylthioethyl. Methoxymethyl is a preferred value of R$_1$.

Typically R$_2$ is H and at least one, but preferably both of R$_3$ and R$_4$ are methyl. When one of R$_3$ and R$_4$ is H, the other may be methyl, ethyl or n- or iso-propyl. When one of R$_3$ and R$_4$ is methyl, the other may be H or ethyl but is preferably also methyl. R$_2$ also includes $C_{1-4}$ alkoxymethyl and benzyloxymethyl in which the phenyl ring of the benzyl group optionally carries an alkoxy substituent, e.g. a methoxy substituent. Such values of R$_2$ provide compounds of formula (1) that are believed to be pro-pesticidal compounds.

Typically R$_5$ is H, methyl, hydroxymethyl, methoxymethyl, 1-methoxyethyl, tert-butyldimethylsiloxymethyl, 3-cyanopropyl, 3-methoxypropyl, 3-(1,2,4-triazol-1-yl)-propyl, 3-methylthiopropyl, 3-methanesulphinylpropyl or 3-methanesulphonylpropyl. Of particular interest are compounds where $R_5$ is methyl, methoxymethyl or cyanopropyl.

In one aspect the invention provides a compound of the general formula (1)

wherein

X, Y and Z are independently H, halogen, $C_{1-4}$ alkyl (e.g. methyl), halo($C_{1-4}$)alkyl (e.g. trifluoromethyl), $C_{2-4}$ alkenyl, halo($C_{2-4}$)alkenyl, $C_{2-4}$ alkynyl, halo($C_{2-4}$)alkynyl, $C_{1-4}$ alkoxy (e.g. methoxy), halo($C_{1-4}$)alkoxy (e.g. trifluoromethoxy), —S(O)$_n$($C_{1-4}$)alkyl where n is 0, 1 or 2 and the alkyl group is optionally substituted with fluoro (e.g. methylthio, tri-fluoromethylsulphonyl), —OSO$_2$($C_{1-4}$)alkyl where the alkyl group is optionally substituted with fluoro (e.g. trifluoromethylsulphonyloxy), cyano, nitro, $C_{1-4}$ alkoxycarbonyl, —CONR'R", —COR' or —NR'COR" where R' and R" are independently H or $C_{1-4}$ alkyl (e.g. —NHCOCH$_3$), provided that at least one of X and Z is other than H;

$R_1$ is alkoxyalkyl, alkylthioalkyl, alkylsulphinylalkyl or alkylsulphonylalkyl in which the total number of carbon atoms is 2 or 3 (e.g. methoxymethyl, methylthiomethyl, ethoxymethyl, 2-methoxyethyl and 2-methylthioethyl);

$R_2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy;

$R_3$ and $R_4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R_3$ and $R_4$ join with the carbon atom to which they are attached to form a 3 or 4 membered carbocyclic ring optionally containing one O, S or N atom and optionally substituted with halo or $C_{1-4}$ alkyl; and $R_5$ is H, $C_{1-4}$ alkyl or $C_{3-6}$ cycloalkyl in which the alkyl or cycloalkyl group is optionally substituted with halo, hydroxy, $C_{1-6}$ alkoxy, $C_{1-6}$ alkylthio, cyano, $C_{1-4}$ alkylcarbonyloxy, aminocarbonyloxy or mono- or di($C_{1-4}$) alkylaminocarbonyloxy, tri($C_{1-4}$)alkylsilyloxy, optionally substituted phenoxy, optionally substituted thienyloxy, optionally substituted benzyloxy or optionally substituted thienylmethoxy, or $R_5$ is optionally substituted phenyl, optionally substituted thienyl or optionally substituted benzyl, in which the optionally substituted phenyl and thienyl rings of the $R_5$ values are optionally substituted with one, two or three substituents selected from halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R", —NHCOR''', —NHCONR'''R", —CONR'''R", —SO$_2$R''', —OSO$_2$R''', —COR''', —CR'''=NR" or —N=CR'''R", in which R''' and R" are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

In another aspect the invention provides a compound of the general formula (1) wherein X, Y and Z are all chloro or methyl, or X and Z are both chloro or bromo and Y is H or methyl, or X and Z are both methyl or methoxy and Y is H, chloro, bromo or alkylthio, or X is methoxy, Y is H and Z is cyano or chloro, or X is methyl, Y is H and Z is ethyl, or X is chloro, bromo or trifluoromethyl and both Y and Z are H; $R_1$ is methoxymethyl, methylthiomethyl, ethoxymethyl, 2-methoxyethyl or 2-methythioethyl; $R_2$ is H; $R_3$ and $R_4$ are both methyl; and $R_5$ is H, methyl, hydroxymethyl, methoxymethyl, 1-methoxyethyl, tert-butyldimethylsiloxymethyl, 3-cyanopropyl, 3-methoxypropyl, 3-(1,2,4-triazol-1-yl)propyl, 3-methylthiopropyl, 3-methanesulphinylpropyl or 3-methanesulphonylpropyl. Preferably $R_1$ is methoxymethyl. Preferably $R_5$ is methyl, methoxymethyl or 3-cyanopropyl.

Compounds that form part of the invention are illustrated in Tables 1 to 41 below. Characterisation data are given in Table 42 and later in the Examples.

The compounds in Table 1 are of the general formula (1) where $R_1$ is methoxy-methyl, $R_2$ is H, $R_3$ and $R_4$ are both methyl, $R_5$ is methyl and X, Y and Z have the values given in the table.

TABLE 1

| Compound No | X | Y | Z |
|---|---|---|---|
| 1 | Cl | Cl | CN |
| 2 | Cl | Cl | Cl |
| 3 | CH$_3$ | CH$_3$ | CH$_3$ |
| 4 | Cl | H | Cl |
| 5 | Cl | CH$_3$ | Cl |
| 6 | Br | H | Br |
| 7 | Br | CH$_3$ | Br |
| 8 | CH$_3$ | H | CH$_3$ |
| 9 | CH$_3$ | Cl | CH$_3$ |
| 10 | CH$_3$ | Br | CH$_3$ |
| 11 | CH$_3$ | CH$_3$S | CH$_3$ |
| 12 | CH$_3$O | H | CH$_3$O |
| 13 | CH$_3$O | Cl | CH$_3$O |
| 14 | CH$_3$O | Br | CH$_3$O |
| 15 | CH$_3$O | CH$_3$S | CH$_3$O |
| 16 | CH$_3$O | H | CN |
| 17 | CH$_3$O | H | Cl |
| 18 | CH$_3$ | H | C$_2$H$_5$ |
| 19 | Cl | H | H |
| 20 | Br | H | H |
| 21 | CF$_3$ | H | H |
| 22 | Br | Cl | H |
| 23 | Br | Br | H |
| 24 | Br | F | H |
| 25 | Br | CN | H |
| 26 | Br | CF$_3$O | H |
| 27 | Br | CH$_3$S | H |
| 28 | Br | HC≡C— | H |
| 29 | Br | CH$_2$=CH— | H |
| 30 | Br | CH$_3$O | H |
| 31 | Br | COCH$_3$ | H |
| 32 | Br | CF$_3$ | H |
| 33 | F | H | H |
| 34 | CN | H | H |
| 35 | CH$_3$ | H | H |
| 36 | CH$_3$CO | H | H |
| 37 | CH$_3$O | H | H |
| 38 | CF$_3$O | H | H |
| 39 | CH$_3$S | H | H |
| 40 | HC≡C— | H | H |
| 41 | H$_2$C=CH— | H | H |
| 42 | F | H | F |
| 43 | F | H | Cl |
| 44 | F | H | Br |
| 45 | F | H | CH$_3$O |
| 46 | F | H | CH$_3$CO |
| 47 | F | H | CN |
| 48 | F | H | CH$_3$ |
| 49 | F | H | CF$_3$O |
| 50 | F | H | CF$_3$ |
| 51 | F | H | CH$_3$S |
| 52 | F | H | COOCH$_3$ |
| 53 | Cl | H | Br |

TABLE 1-continued

| Compound No | X | Y | Z |
|---|---|---|---|
| 54 | Cl | H | $CH_3CO$ |
| 55 | Cl | H | $CH_3$ |
| 56 | Cl | H | CN |
| 57 | Cl | H | $CF_3O$ |
| 58 | Cl | H | $CF_3$ |
| 59 | Cl | H | $CH_3S$ |
| 60 | Cl | H | $COOCH_3$ |
| 61 | Cl | H | $CON(CH_3)_2$ |
| 62 | Cl | H | $NHCOOCH_3$ |
| 63 | Cl | H | $OSO_2CH_3$ |
| 64 | Cl | H | $HC\equiv C-$ |
| 65 | Cl | H | $CH_2=CH-$ |
| 66 | Br | H | $CH_3$ |
| 67 | Br | H | CN |
| 68 | CN | H | CN |
| 69 | CN | H | $CH_3$ |
| 70 | CN | H | $CF_3O$ |
| 71 | $CF_3O$ | H | $CF_3O$ |
| 72 | $CF_3$ | H | $CF_3$ |
| 73 | $CH_3$ | H | $CH_3O$ |
| 74 | F | F | H |
| 75 | F | Cl | H |
| 76 | F | Br | H |
| 77 | F | $CH_3O$ | H |
| 78 | F | CN | H |
| 79 | F | $CH_3$ | H |
| 80 | Cl | Cl | H |
| 81 | Cl | F | H |
| 82 | Cl | Br | H |
| 83 | Cl | CN | H |
| 84 | Cl | $CH_3$ | H |
| 85 | Cl | $CH_3O$ | H |
| 86 | Cl | $CF_3O$ | H |
| 87 | Cl | $CH_3S$ | H |
| 88 | Cl | $CH_3SO_2O$ | H |
| 89 | Cl | $CH_3CO$ | H |
| 90 | CN | F | H |
| 91 | CN | Cl | H |
| 92 | CN | $CH_3O$ | H |
| 93 | $CH_3O$ | $CH_3O$ | H |
| 94 | $CH_3O$ | Cl | H |
| 95 | $CH_3O$ | CN | H |
| 96 | $CH_3CO$ | Cl | H |
| 97 | $CF_3O$ | Cl | H |
| 98 | $CF_3O$ | CN | H |
| 99 | $CH_3S$ | Cl | H |
| 100 | $CH_3S$ | F | H |
| 101 | $CH_3S$ | $CH_3$ | H |
| 102 | $CH_3SO_2O$ | Cl | H |
| 103 | Cl | Cl | F |
| 104 | Cl | Cl | Br |
| 105 | Cl | Cl | $CH_3O$ |
| 106 | Cl | Cl | $CH_3CO$ |
| 107 | Cl | Cl | $CH_3S$ |
| 108 | Cl | F | Cl |
| 109 | Cl | $CH_3O$ | Cl |
| 110 | Cl | $CF_3O$ | Cl |
| 11 | Cl | $CH_3SO$ | Cl |
| 112 | Cl | $CH_3SO_2$ | Cl |
| 113 | Cl | $OSO_2CH_3$ | Cl |
| 114 | Cl | $CH_3CO$ | Cl |
| 115 | Cl | $CO_2CH_3$ | Cl |
| 116 | Cl | $CON(CH_3)_2$ | Cl |
| 117 | Cl | $HC\equiv C-$ | Cl |
| 118 | Cl | $CH_2=CH-$ | Cl |
| 119 | Cl | $NHCO_2CH_3$ | Cl |
| 120 | F | F | F |
| 121 | F | F | CN |
| 122 | F | F | $CH_3$ |
| 123 | F | F | $CH_3O$ |
| 124 | F | $CH_3O$ | F |
| 125 | F | $CF_3O$ | F |
| 126 | F | $CH_3SO$ | F |
| 127 | F | $CH_3SO_2$ | F |
| 128 | F | $OSO_2CH_3$ | F |
| 129 | F | $CH_3CO$ | F |
| 130 | F | $CO_2CH_3$ | F |
| 131 | $CH_3O$ | $CH_3O$ | $CH_3O$ |
| 132 | $CH_3O$ | $CH_3O$ | Cl |
| 133 | $CH_3O$ | $CH_3O$ | $CH_3$ |
| 134 | Cl | CN | Cl |

TABLE 2

Table 2 consists of 134 compounds of the general formula (1), where $R_1$ is ethoxymethyl, $R_2$ is hydrogen, $R_3$ and $R_4$ are both methyl, $R_5$ is methyl and X, Y and Z have the values listed in Table 1. Thus compound 1 of Table 2 is the same as compound 1 of Table 1 except that in compound 1 of Table 2 $R_1$ is ethoxymethyl instead of methoxymethyl. Similarly, compounds 2 to 134 of Table 2 are the same as compounds 2 to 134 of Table 1, respectively, except that in the compounds of Table 2 $R_1$ is ethoxymethyl instead of methoxymethyl.

TABLE 3

Table 3 consists of 134 compounds of the general formula (1), where $R_1$ is methylthiomethyl, $R_2$ is hydrogen, $R_3$ and $R_4$ are both methyl, and $R_5$ is methyl and X, Y and Z have the values listed in Table 1. Thus compound 1 of Table 3 is the same as compound 1 of Table 1 except that in compound 1 of Table 3 $R_1$ is methylthiomethyl instead of methoxymethyl. Similarly, compounds 2 to 134 of Table 3 are the same as compounds 2 to 134 of Table 1, respectively, except that in the compounds of Table 3 $R_1$ is methylthiomethyl instead of methoxymethyl.

TABLE 4

Table 4 consists of 134 compounds of the general formula (1), where $R_1$ is 2-methoxyethyl, $R_2$ is hydrogen, $R_3$ and $R_4$ are both methyl, $R_5$ is methyl and X, Y and Z have the values listed in Table 1. Thus compound 1 of Table 4 is the same as compound 1 of Table 1 except that in compound 1 of Table 4 $R_1$ is 2-methoxyethyl instead of methoxymethyl. Similarly, compounds 2 to 134 of Table 4 are the same as compounds 2 to 134 of Table 1, respectively, except that in the compounds of Table 4 $R_1$ is 2-methoxyethyl instead of methoxymethyl.

TABLE 5

Table 5 consists of 134 compounds of the general formula (1), where $R_1$ is 2-methylthioethyl, $R_2$ is hydrogen, $R_3$ and $R_4$ are both methyl, $R_5$ is methyl and X, Y and Z have the values listed in Table 1. Thus compound 1 of Table 5 is the same as compound 1 of Table 1 except that in compound 1 of Table 5 $R_1$ is 2-methylthioethyl instead of methoxymethyl. Similarly, compounds 2 to 134 of Table 5 are the same as compounds 2 to 134 of Table 1, respectively, except that in the compounds of Table 4 $R_1$ is 2-methylthioethyl instead of methoxymethyl.

TABLE 6

Table 6 consists of 134 compounds of the general formula (1), where $R_1$ is methoxymethyl, $R_2$ is hydrogen, $R_3$ and $R_4$ are both methyl, $R_5$ is H and X, Y and Z have the values listed in Table 1. Thus compound 1 of Table 6 is the same as compound 1 of Table 1 except that in compound 1 of Table 6 $R_5$ is H instead of methyl. Similarly, compounds 2 to 134 of Table 6 are the same as compounds 2 to 134 of Table 1, respectively, except that in the compounds of Table 6 $R_5$ is H instead of methyl.

TABLE 7

Table 7 consists of 134 compounds of the general formula (1), where $R_1$ is ethoxymethyl, $R_2$ is hydrogen, $R_3$ and $R_4$ are both methyl, $R_5$ is H and X, Y and Z have the values listed in Table 1 for compounds 1 to 134. Thus compound 1 of Table 7 is the same as compound 1 of Table 2 except that in compound 1 of Table 7 $R_5$ is H instead of methyl. Similarly, compounds 2 to 134 of Table 7 are the same as compounds 2 to 134 of Table 2, respectively, except that in the compounds of Table 7 $R_5$ is H instead of methyl.

TABLE 8

Table 8 consists of 134 compounds of the general formula (1), where $R_1$ is methylthiomethyl, $R_2$ is hydrogen, $R_3$ and $R_4$ are both methyl, and $R_5$ is H and X, Y and Z have the values listed in Table 1. Thus compound 1 of Table 8 is the same as compound 1 of Table 3 except that in compound 1 of Table 8 $R_5$ is H instead of methyl. Similarly, compounds 2 to 134 of Table 8 are the same as compounds 2 to 134 of Table 3, respectively, except that in the compounds of Table 8 $R_1$ is H instead of methyl.

TABLE 9

Table 9 consists of 134 compounds of the general formula (1), where $R_1$ is 2-methoxyethyl, $R_2$ is hydrogen, $R_3$ and $R_4$ are both methyl, $R_5$ is H and X, Y and Z have the values listed in Table 1. Thus compound 1 of Table 9 is the same as compound 1 of Table 4 except that in compound 1 of Table 9 $R_5$ is H instead of methyl. Similarly, compounds 2 to 134 of Table 9 are the same as compounds 2 to 134 of Table 4, respectively, except that in the compounds of Table 9 $R_5$ is H instead of methyl.

TABLE 10

Table 10 consists of 134 compounds of the general formula (1), where $R_1$ is 2-methylthio-ethyl, $R_2$ is hydrogen, $R_3$ and $R_4$ are both methyl, $R_5$ is H and X, Y and Z have the values listed in Table 1. Thus compound 1 of Table 10 is the same as compound 1 of Table 5 except that in compound 1 of Table 10 $R_5$ is H instead of methyl. Similarly, compounds 2 to 134 of Table 10 are the same as compounds 2 to 134 of Table 5, respectively, except that in the compounds of Table 10 $R_5$ is H instead of methyl.

TABLE 11

Table 11 consists of 134 compounds of the general formula (1), where $R_1$ is methoxymethyl, $R_2$ is hydrogen, $R_3$ and $R_4$ are both methyl, $R_5$ is hydroxymethyl and X, Y and Z have the values listed in Table 1. Thus compound 1 of Table 11 is the same as compound 1 of Table 1 except that in compound 1 of Table 11 $R_5$ is hydroxymethyl instead of methyl. Similarly, compounds 2 to 134 of Table 11 are the same as compounds 2 to 134 of Table 1, respectively, except that in the compounds of Table 11 $R_5$ is hydroxymethyl instead of methyl.

TABLE 12

Table 12 consists of 134 compounds of the general formula (1), where $R_1$ is ethoxymethyl, $R_2$ is hydrogen, $R_3$ and $R_4$ are both methyl, $R_5$ is hydroxymethyl and X, Y and Z have the values listed in Table 1. Thus compound 1 of Table 12 is the same as compound 1 of Table 2 except that in compound 1 of Table 12 $R_5$ is hydroxymethyl instead of methyl. Similarly, compounds 2 to 134 of Table 12 are the same as compounds 2 to 134 of Table 2, respectively, except that in the compounds of Table 12 $R_5$ is hydroxymethyl instead of methyl.

TABLE 13

Table 13 consists of 134 compounds of the general formula (1), where $R_1$ is methylthiomethyl, $R_2$ is hydrogen, $R_3$ and $R_4$ are both methyl, and $R_5$ is hydroxymethyl and X, Y and Z have the values listed in Table 1. Thus compound 1 of Table 13 is the same as compound 1 of Table 3 except that in compound 1 of Table 13 $R_5$ is hydroxymethyl instead of methyl. Similarly, compounds 2 to 134 of Table 13 are the same as compounds 2 to 134 of Table 3, respectively, except that in the compounds of Table 13 $R_1$ is hydroxymethyl instead of methyl.

TABLE 14

Table 14 consists of 134 compounds of the general formula (1), where $R_1$ is 2-methoxyethyl, $R_2$ is hydrogen, $R_3$ and $R_4$ are both methyl, $R_5$ is hydroxymethyl and X, Y and Z have the values listed in Table 1. Thus compound 1 of Table 14 is the same as compound 1 of Table 4 except that in compound 1 of Table 14 $R_5$ is hydroxymethyl instead of methyl. Similarly, compounds 2 to 134 of Table 14 are the same as compounds 2 to 134 of Table 4, respectively, except that in the compounds of Table 14 $R_5$ is hydroxymethyl instead of methyl.

TABLE 15

Table 15 consists of 134 compounds of the general formula (1), where $R_1$ is 2-methylthioethyl, $R_2$ is hydrogen, $R_3$ and $R_4$ are both methyl, $R_5$ is hydroxymethyl and X, Y and Z have the values listed in Table 1. Thus compound 1 of Table 15 is the same as compound 1 of Table 5 except that in compound 1 of Table 15 $R_5$ is hydroxymethyl instead of methyl. Similarly, compounds 2 to 134 of Table 15 are the same as compounds 2 to 134 of Table 5, respectively, except that in the compounds of Table 15 $R_5$ is hydroxymethyl instead of methyl.

TABLE 16

Table 16 consists of 134 compounds of the general formula (1), where $R_1$ is methoxymethyl, $R_2$ is hydrogen, $R_3$ and $R_4$ are both methyl, $R_5$ is methoxymethyl and X, Y and Z have the values listed in Table 1. Thus compound 1 of Table 16 is the same as compound 1 of Table 1 except that in compound 1 of Table 16 $R_5$ is methoxymethyl instead of methyl. Similarly, compounds 2 to 134 of Table 16 are the same as compounds 2 to 134 of Table 1, respectively, except that in the compounds of Table 16 $R_5$ is methoxymethyl instead of methyl.

TABLE 17

Table 17 consists of 134 compounds of the general formula (1), where $R_1$ is ethoxymethyl, $R_2$ is hydrogen, $R_3$ and $R_4$ are both methyl, $R_5$ is methoxymethyl and X, Y and Z have the values listed in Table 1. Thus compound 1 of Table 17 is the same as compound 1 of Table 2 except that compound 1 of Table 17 $R_5$ is methoxymethyl instead of methyl. Similarly, compounds 2 to 134 of Table 17 are the same as compounds 2 to 134 of Table 2, respectively, except that in the compounds of Table 17 $R_5$ is methoxymethyl instead of methyl.

TABLE 18

Table 18 consists of 134 compounds of the general formula (1), where $R_1$ is methylthiomethyl, $R_2$ is hydrogen, $R_3$ and $R_4$ are both methyl, and $R_5$ is methoxymethyl and X, Y and Z have the values listed in Table 1. Thus compound 1 of Table 18 is the same as compound 1 of Table 3 except that in compound 1 of Table 18 $R_5$ is methoxymethyl instead of methyl. Similarly, compounds 2 to 134 of Table 18 are the same as compounds 2 to 134 of Table 3, respectively, except that in the compounds of Table 18 $R_1$ is methoxymethyl instead of methyl.

TABLE 19

Table 19 consists of 134 compounds of the general formula (1), where $R_1$ is 2-methoxyethyl, $R_2$ is hydrogen, $R_3$ and $R_4$ are both methyl, $R_5$ is methoxymethyl and X, Y and Z have the values listed in Table 1. Thus compound 1 of Table 19 is the same as compound 1 of Table 4 except that in compound 1 of Table 19 $R_5$ is methoxymethyl instead of methyl. Similarly, compounds 2 to 134 of Table 19 are the same as compounds 2 to 134 of Table 4, respectively, except that in the compounds of Table 19 $R_5$ is methoxymethyl instead of methyl.

TABLE 20

Table 20 consists of 134 compounds of the general formula (1), where $R_1$ is 2-methylthioethyl, $R_2$ is hydrogen, $R_3$ and $R_4$ are both methyl, $R_5$ is methoxymethyl and X, Y and Z have the values listed in Table 1. Thus compound 1 of Table 20 is the same as compound 1 of Table 5 except that in compound 1 of Table 20 $R_5$ is methoxymethyl instead of methyl. Similarly, compounds 2 to 134 of Table 20 are the same as compounds 2 to 134 of Table 5, respectively, except that in the compounds of Table 20 $R_5$ is methoxymethyl instead of methyl.

TABLE 21

Table 21 consists of 134 compounds of the general formula (1), where $R_1$ is methoxymethyl, $R_2$ is hydrogen, $R_3$ and $R_4$ are both methyl, $R_5$ is tert-butyldimethylsilyloxymethyl and X, Y and Z have the values listed in Table 1. Thus compound 1 of Table 21 is the same as compound 1 of Table 1 except that in compound 1 of Table 21 $R_5$ is tert-butyldimethylsilyloxymethyl instead of methyl. Similarly, compounds 2 to 134 of Table 21 are the same as compounds 2 to 134 of Table 1, respectively, except that in the compounds of Table 21 $R_5$ is tert-butyldimethylsilyloxymethyl instead of methyl.

TABLE 22

Table 22 consists of 134 compounds of the general formula (1), where $R_1$ is ethoxymethyl, $R_2$ is hydrogen, $R_3$ and $R_4$ are both methyl, $R_5$ is tert-butyldimethylsilyloxymethyl and X, Y and Z have the values listed in Table 1. Thus compound 1 of Table 22 is the same as compound 1 of Table 2 except that in compound 1 of Table 22 $R_5$ is tert-butyldimethylsilyloxymethyl instead of methyl. Similarly, compounds 2 to 134 of Table 22 are the same as compounds 2 to 134 of Table 2, respectively except that in the compounds of Table 22 $R_5$ is tert-butyldimethylsilyloxymethyl instead of methyl.

TABLE 23

Table 23 consists of 134 compounds of the general formula (1), where $R_1$ methylthiomethyl, $R_2$ is hydrogen, $R_3$ and $R_4$ are both methyl, and $R_5$ is tert-butyldimethylsilyloxymethyl and X, Y and Z have the values listed in Table 1. Thus compound 1 of Table 23 is the same as compound 1 of Table 3 except that in compound 1 of Table 23 $R_5$ is tert-butyldimethylsilyloxymethyl instead of methyl. Similarly, compounds 2 to 134 of Table 23 are the same as compounds 2 to 134 of Table 3, respectively, except that in the compounds of Table 23 $R_1$ is tert-butyldimethylsilyloxymethyl instead of methyl.

TABLE 24

Table 24 consists of 134 compounds of the general formula (1), where $R_1$ is 2-methoxyethyl, $R_2$ is hydrogen, $R_3$ and $R_4$ are both methyl, $R_5$ is tert-butyldimethylsilyloxymethyl and X, Y and Z have the values listed in Table 1. Thus compound 1 of Table 24 is the same as compound 1 of Table 4 except that in compound 1 of Table 24 $R_5$ is tert-butyldimethylsilyloxymethyl instead of methyl. Similarly, compounds 2 to 134 of Table 24 are the same as compounds 2 to 134 of Table 4, respectively, except that in the compounds of Table 24 $R_5$ is tert-butyldimethylsilyloxymethyl instead of methyl.

TABLE 25

Table 25 consists of 134 compounds of the general formula (1), where $R_1$ is 2-methylthioethyl, $R_2$ is hydrogen, $R_3$ and $R_4$ are both methyl, $R_5$ is tert-butyldimethylsilyloxymethyl and X, Y and Z have the values listed in Table 1. Thus compound 1 of Table 25 is the same as compound 1 of Table 5 except that in compound 1 of Table 25 $R_5$ is tert-butyldimethylsilyloxymethyl instead of methyl. Similarly, compounds 2 to 134 of Table 25 are the same as compounds 2 to 134 of Table 5, respectively, except that in the compounds of Table 25 $R_5$ is tert-butyldimethylsilyloxymethyl instead of methyl.

TABLE 26

Table 26 consists of 134 compounds of the general formula (1), where $R_1$ is methoxymethyl, $R_2$ is hydrogen, $R_3$ and $R_4$ are both methyl, $R_5$ is 1-methoxyethyl and X, Y and Z have the values listed in Table 1. Thus compound 1 of Table 26 is the same as compound 1 of Table 1 except that in compound 1 of Table 26 $R_5$ is 1-methoxyethyl instead of methyl. Similarly, compounds 2 to 134 of Table 26 are the same as compounds 2 to 134 of Table 1, respectively, except that in the compounds of Table 26 $R_5$ is 1-methoxyethyl instead of methyl

TABLE 27

Table 27 consists of 134 compounds of the general formula (1), where $R_1$ is ethoxymethyl, $R_2$ is hydrogen, $R_3$ and $R_4$ are both methyl, $R_5$ is 1-methoxyethyl and X, Y and Z have the values listed in Table 1. Thus compound 1 of Table 27 is the same as compound 1 of Table 2 except that in compound 1 of Table 27 $R_5$ is 1-methoxyethyl instead of methyl. Similarly, compounds 2 to 134 of Table 27 are the same as compounds 2 to 134 of Table 2, respectively, except that in the compounds of Table 27 $R_5$ is 1-methoxyethyl instead of methyl.

TABLE 28

Table 28 consists of 134 compounds of the general formula (1), where $R_1$ is methylthiomethyl, $R_2$ is hydrogen, $R_3$ and $R_4$ are both methyl, and $R_5$ is 1-methoxyethyl and X, Y and Z have the values listed in Table 1. Thus compound 1 of Table 28 is the same as compound 1 of Table 3 except that in compound 1 of Table 28 $R_5$ is 1-methoxyethyl instead of methyl. Similarly, compounds 2 to 134 of Table 28 are the same as compounds 2 to 134 of Table 3, respectively, except that in the compounds of Table 28 $R_1$ is 1-methoxyethyl instead of methyl.

TABLE 29

Table 29 consists of 134 compounds of the general formula (1), where $R_1$ is 2-methoxy-ethyl, $R_2$ is hydrogen, $R_3$ and $R_4$ are both methyl, $R_5$ is 1-methoxyethyl and X, Y and Z have the values listed in Table 1. Thus compound 1 of Table 29 is the same as compound 1 of Table 4 except that in compound 1 of Table 29 $R_5$ is 1-methoxyethyl instead of methyl. Similarly, compounds 2 to 134 of Table 29 are the same as compounds 2 to 134 of Table 4, respectively, except that in the compounds of Table 29 $R_5$ is l-methoxyethyl instead of methyl.

TABLE 30

Table 30 consists of 134 compounds of the general formula (1), where $R_1$ is 2-methylthioethyl, $R_2$ is hydrogen, $R_3$ and $R_4$ are both methyl, $R_5$ is 1-methoxyethyl and X, Y and Z have the values listed in Table 1. Thus compound 1 of Table 30 is the same as compound 1 of Table 5 except that in compound I of Table 30 $R_5$ is 1-methoxyethyl instead of methyl. Similarly, compounds 2 to 134 of Table 30 are the same as compounds 2 to 134 of Table 5, respectively, except that in the compounds of Table 30 $R_5$ is 1-methoxyethyl instead of methyl.

TABLE 31

Table 31 consists of 134 compounds of the general formula (1), where $R_1$ is methoxy-methyl, $R_2$ is hydrogen, $R_3$ and $R_4$ are both methyl, $R_5$ is 3-cyanopropyl and X, Y and Z have the values listed in Table 1. Thus compound 1 of Table 31 is the same as compound 1 of Table 1 except that in compound 1 of Table 31 $R_5$ is 3-cyanopropyl instead of methyl. Similarly, compounds 2 to 134 of Table 31 are the same as compounds 2 to 134 of Table 1, respectively, except that in the compounds of Table 31 $R_5$ is 3-cyanopropyl instead of methyl.

TABLE 32

Table 32 consists of 134 compounds of the general formula (1), where $R_1$ is ethoxymethyl, $R_2$ is hydrogen, $R_3$ and $R_4$ are both methyl, $R_5$ is 3-cyanopropyl and X, Y and Z have the values listed in Table 1. Thus compound 1 of Table 32 is the same as compound 1 of Table 2 except that
in compound 1 of Table 32 $R_5$ is 3-cyanopropyl instead of methyl. Similarly, compounds 2 to 134 of Table 32 are the same as compounds 2 to 134 of Table 2, respectively, except that in the compounds of Table 32 $R_5$ is 3-cyanopropyl instead of methyl.

TABLE 33

Table 33 consists of 134 compounds of the general formula (1), where $R_1$ is methylthiomethyl, $R_2$ is hydrogen, $R_3$ and $R_4$ are both methyl, and $R_5$ is 3-cyanopropyl and X, Y and Z have the values listed in Table 1. Thus compound 1 of Table 33 is the same as compound 1 of Table 3 except that in compound 1 of Table 33 $R_5$ is 3-cyanopropyl instead of methyl. Similarly, compounds 2 to 134 of Table 33 are the same as compounds 2 to 134 of Table 3, respectively, except that in the compounds of Table 33 $R_1$ is 3-cyanopropyl instead of methyl.

TABLE 34

Table 34 consists of 134 compounds of the general formula (1), where $R_1$ is 2-methoxyethyl, $R_2$ is hydrogen, $R_3$ and $R_4$ are both methyl, $R_5$ is 3-cyanopropyl and X, Y and Z have the values listed in Table 1. Thus compound 1 of Table 34 is the same as compound 1 of Table 4 except that
in compound 1 of Table 34 $R_5$ is 3-cyanopropyl instead of methyl. Similarly, compounds 2 to 134 of Table 34 are the same as compounds 2 to 134 of Table 4, respectively, except that in the compounds of Table 34 $R_5$ is 3-cyanopropyl instead of methyl.

TABLE 35

Table 35 consists of 134 compounds of the general formula (1), where $R_1$ is 2-methylthioethyl, $R_2$ is hydrogen, $R_3$ and $R_4$ are both methyl, $R_5$ is 3-cyanopropyl and X, Y and Z have the values listed in Table 1. Thus compound 1 of Table 35 is the same as compound 1 of Table 5 except that
in compound 1 of Table 35 $R_5$ is 3-cyanopropyl instead of methyl. Similarly, compounds 2 to 134 of Table 35 are the same as compounds 2 to 134 of Table 5, respectively, except that in the compounds of Table 35 $R_5$ is 3-cyanopropyl instead of methyl.

TABLE 36

Table 36 consists of 134 compounds of the general formula (1), where $R_1$ is methoxymethyl, $R_2$ is hydrogen, $R_3$ and $R_4$ are both methyl, $R_5$ is 3-chloropropyl and X, Y and Z have the values listed in Table 1. Thus compound 1 of Table 36 is the same as compound 1 of Table 1 except that
in compound 1 of Table 36 $R_5$ is 3-chloropropyl instead of methyl. Similarly, compounds 2 to 134 of Table 36 are the same as compounds 2 to 134 of Table 1, respectively, except that in the compounds of Table 36 $R_5$ is 3-chloropropyl instead of methyl.

TABLE 37

Table 37 consists of 134 compounds of the general formula (1), where $R_1$ is methoxymethyl, $R_2$ is hydrogen, $R_3$ and $R_4$ are both methyl, $R_5$ is 3-methylthiopropyl and X, Y and Z have the values listed in Table 1. Thus compound 1 of Table 37 is the same as compound 1 of Table 1 except that in compound 1 of Table 37 $R_5$ is 3-methylthiopropyl instead of methyl. Similarly, compounds 2 to 134 of Table 37 are the same as compounds 2 to 134 of Table 1, respectively, except that in the compounds of Table 37 $R_5$ is 3-methylthiopropyl instead of methyl.

TABLE 38

Table 38 consists of 134 compounds of the general formula (1), where $R_1$ is methoxymethyl, $R_2$ is hydrogen, $R_3$ and $R_4$ are both methyl, $R_5$ is 3-methanesulphonylpropyl and X, Y and Z have the values listed in Table 1. Thus compound 1 of Table 38 is the same as compound 1 of Table 1 except that in compound 1 of Table 38 $R_5$ is 3-methanesulphinylpropyl instead of methyl. Similarly, compounds 2 to 134 of Table 38 are the same as compounds 2 to 134 of Table 1, respectively, except that in the compounds of Table 38 $R_5$ is 3-methanesulphinylpropyl instead of methyl.

TABLE 39

Table 39 consists of 134 compounds of the general formula (1), where $R_1$ is methoxymethyl, $R_2$ is hydrogen, $R_3$ and $R_4$ are both methyl, $R_5$ is 3-methanesulphonylpropyl and X, Y and Z have the values listed in Table 1. Thus compound 1 of Table 39 is the same as compound 1 of Table 1 except that in compound 1 of Table 39 $R_5$ is 3-methanesulphonylpropyl instead of methyl. Similarly, compounds 2 to 134 of Table 39 are the same as compounds 2 to 134 of Table 1, respectively, except that in the compounds of Table 39 $R_5$ is 3-methanesulphonylpropyl instead of methyl.

TABLE 40

Table 40 consists of 134 compounds of the general formula (1), where $R_1$ is methoxymethyl, $R_2$ is hydrogen, $R_3$ and $R_4$ are both methyl, $R_5$ is 3-(1,2,4-triazol-1-yl)propyl and X, Y and Z have the values listed in Table 1. Thus compound 1 of Table 40 is the same as compound 1 of Table 1 except that in compound 1 of Table 40 $R_5$ is 3-(l,2,4-triazol-1-yl)propyl instead of methyl. Similarly, compounds 2 to 134 of Table 40 are the same as compounds 2 to 134 of Table 1, respectively, except that in the compounds of Table 40 $R_5$ is 3-(1,2,4-triazol-1-yl)propyl instead of methyl.

TABLE 41

Table 41 consists of 134 compounds of the general formula (1), where $R_1$ is methoxymethyl, $R_2$ is hydrogen, $R_3$ and $R_4$ are both methyl, $R_5$ is 3-methoxypropyl and X, Y and Z have the values listed in Table 1. Thus compound 1 of Table 41 is the same as compound 1 of Table 1 except that
in compound 1 of Table 41 $R_5$ is 3-methoxypropyl instead of methyl. Similarly, compounds 2 to 134 of Table 41 are the same as compounds 2 to 134 of Table 1, respectively, except that in the compounds of Table 41 $R_5$ is 3-methoxypropyl instead of methyl.

TABLE 42

| Compound No. | Table No. | $^1$H NMR chemical shifts in ppm from TMS (solvent) or melting point in degrees centigrade |
|---|---|---|
| 4 | 6 | 108-111° C. |

The compounds of formula (1) may be prepared as outlined in Schemes 1 to 7 below in which X, Y, Z, $R_1$, $R_2$, $R_3$, $R_4$ and $R_5$ have the meanings given above, R is $C_{1-4}$ alkyl, L is a leaving group such as a halide, for example iodide, or an alkyl or aryl sulphonyloxy group, for example methylsulphonyloxy and tosyloxy or a triflate, Hal is halogen, $R_a$ is hydrogen or $C_{1-3}$ alkyl, $R_b$ is hydrogen or $C_{1-3}$ alkyl, provided that the total number of carbon atoms in $R_a$ and $R_b$ do not exceed three, $R_c$ is $C_{1-6}$ alkyl, optionally substituted benzyl or optionally substituted thienylmethyl and $R_d$ has the meaning ascribed to it in the text.

As shown in Scheme 1, the compounds of general formula (1) may be prepared by reacting a phenol of the general formula (2) with a compound of the general formula (3) in the presence of a base in a suitable solvent. Typical solvents include N,N-dimethyl-formamide and N-methylpyrrolidin-2-one. Suitable bases include potassium carbonate, sodium hydride or diisopropylethylamine. Phenols of the general formula (2) are either commercially available or are known in the literature or may be prepared from known compounds by standard procedures.

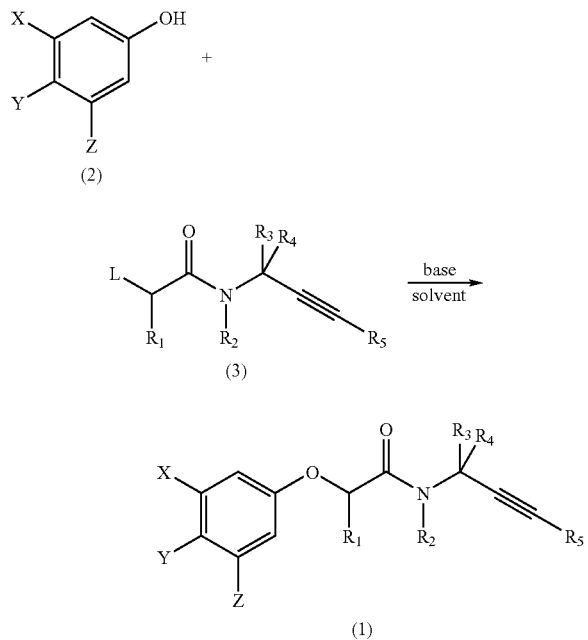

Scheme 1

As shown in Scheme 2, compounds of general formula (3) may be prepared by reacting an amine of the general formula (5) with an acid halide of the general formula (4), or the corresponding acid anhydride, in the presence of a suitable inorganic or organic base, such as potassium carbonate, sodium hydride or diisopropylethylamine, in a solvent such as dichloromethane or tetrahydrofuran.

Scheme 2

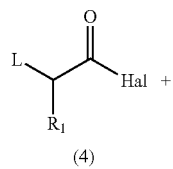

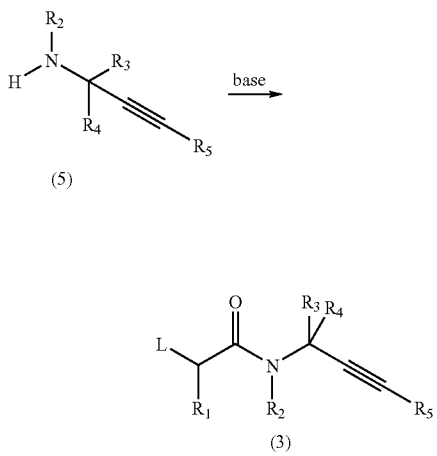

As shown in Scheme 3, amines of the general formula (5), wherein $R_2$ is H, correspond to amines of the general formula (9) and may be prepared by alkylation of a silyl-protected aminoalkyne of the general formula (7) using a suitable base, such as n-butyl lithium, followed by reaction with a suitable alkylating reagent $R_5L$, such as an alkyl iodide, for example, methyl iodide, to form an alkylated compound of the general formula (8). In a similar procedure, a silyl-protected aminoalkyne of the general formula (7) may be reacted with a carbonyl derivative $R_aCOR_b$, for example formaldehyde, using a suitable base, such as n-butyl lithium, to provide an aminoalkyne (8) containing a hydroxyalkyl moiety. The silyl protecting group may then be removed from a compound of the general formula (8) with, for example, an aqueous acid to form an aminoalkyne of the general formula (9). Aminoalkynes of the general formula (9) may be further derivatised, for instance when $R^5$ is a hydroxyalkyl group, for example, by reacting a compound of the general formula (9) with a silylating agent $(R)_3SiCl$, for example t-butyldimethylsilyl chloride, to give a derivative silylated on oxygen of the general formula (9a). In addition, a compound of the general formula (9) may be treated with a base, such as sodium hydride or potassium bis(trimethylsilyl)amide followed by a compound $R_cL$ to give a compound of the general formula (9b). In an alternative sequence, a compound of general formula (8) may be treated with a base, such as sodium or potassium bis(trimethylsilyl)amide, followed by a compound $R_cL$, where L represents a halogen or sulphonate ester such as $OSO_2Me$, or $OSO_2$-4-tolyl, for example ethyl iodide, to give compounds of the general formula (8a), which, after removal of the silyl protecting group, give compounds of the general formula (9b).

Compounds of general formula (8), where $R_5$ is, for example, 3-chloropropyl can be reacted with a metal cyanide salt, such as sodium cyanide, to give compounds of general formula (8b), which can then be hydrolysed, with for example an aqueous acid, to give the amines of general formula (8c). Compounds of general formula (8), where $R_5$ is, for example, 3-chloropropyl can be hydrolysed, with for example an aqueous acid, to give amines of general formula (8d).

Scheme 3

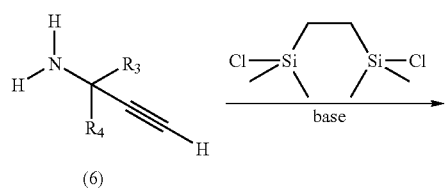

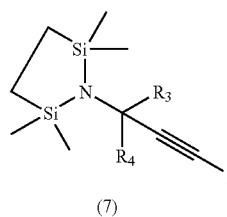

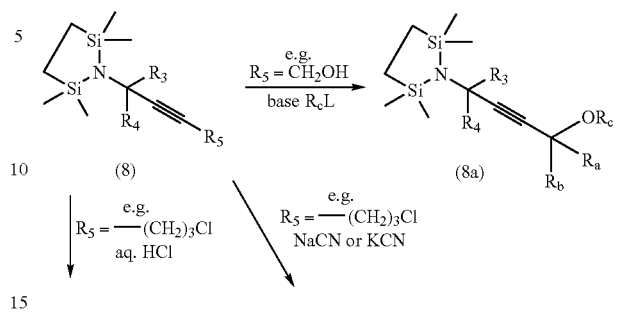

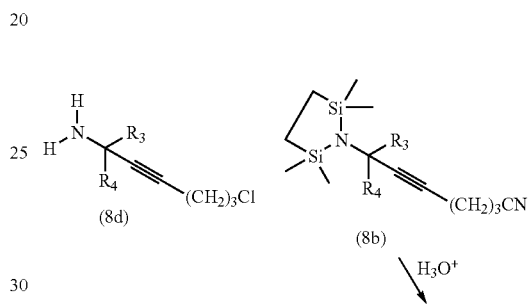

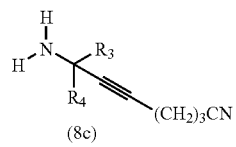

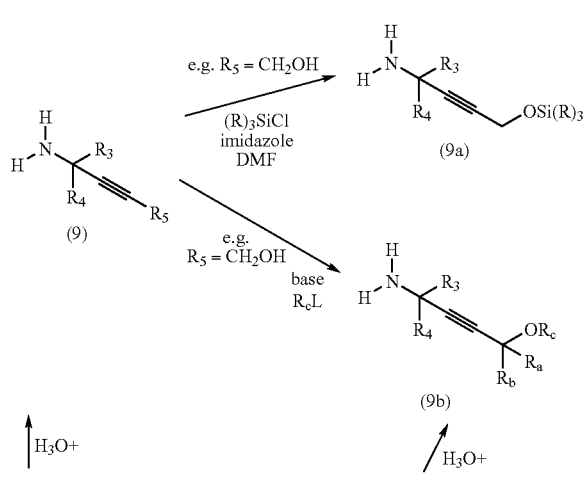

Silyl-protected aminoalkynes of the general formula (7) may be obtained by reacting amines of general formula (6) with 1,2-bis-(chlorodimethylsilyl)ethane in the presence of a suitable base, such as a tertiary organic amine base, for example, triethylamine.

Amines of the general formula (6) are either commercially available or may be prepared by standard literature methods (see, for example, EP-A-0834498).

Alternatively, as shown in Scheme 4, compounds of the general formula (1) may be prepared by condensing a compound of the general formula (11), wherein $R_d$ is H with an amine of the general formula (5) using suitable activating reagents such as 1-hydroxy-benzotriazole and N-(3-dimethylaminopropyl)-N'-ethyl-carbodiimide hydrochloride.

Where $R_2$ is other than hydrogen, the $R_2$ group may be introduced into an aminoalkyne of the general formula (9) by known techniques to form an amine of the general formula (5).

Scheme 4

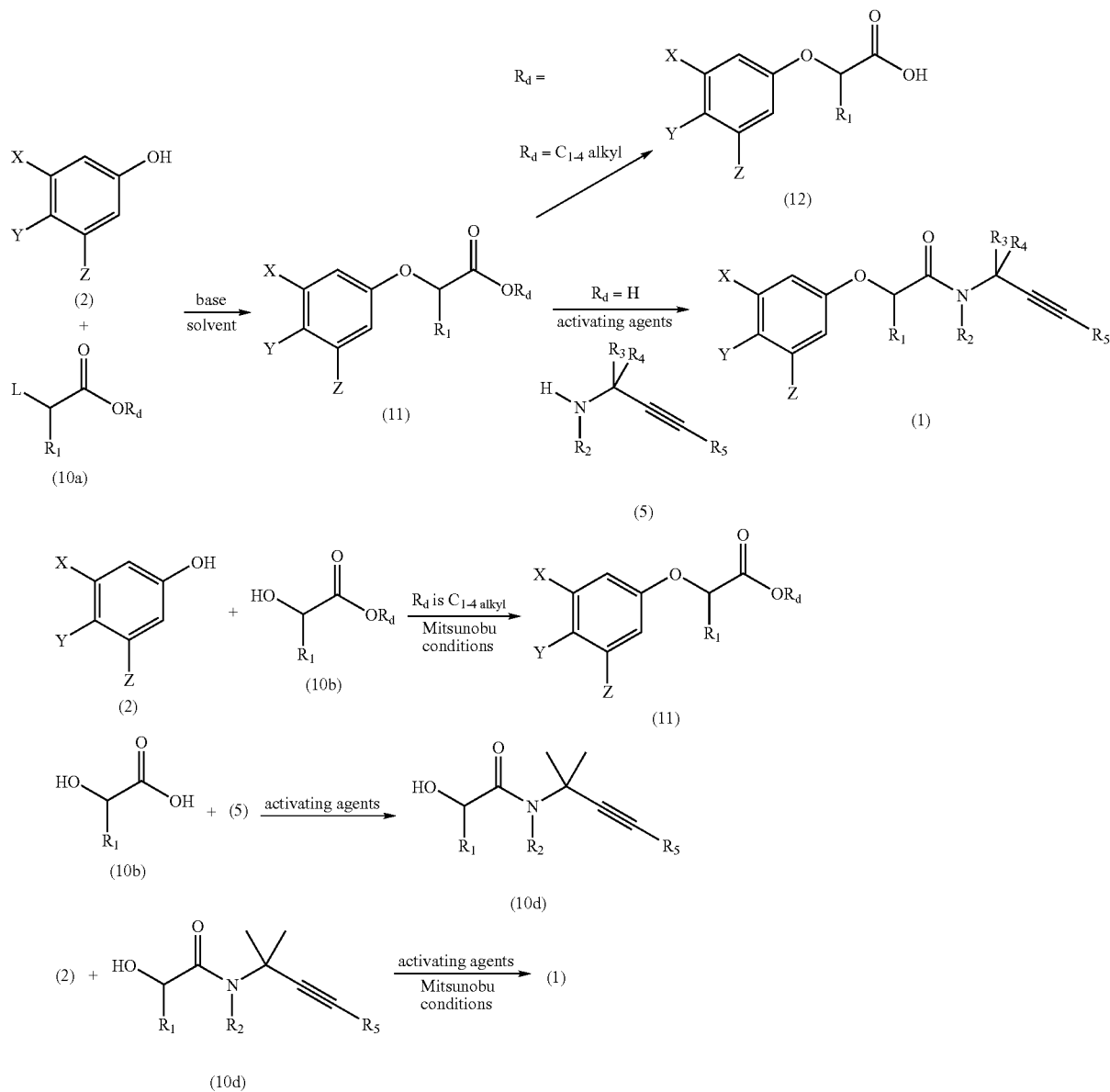

Compounds of the general formula (12) may be prepared by the hydrolysis of the corresponding esters of general formula (11), wherein $R_d$ is $C_{1-4}$ alkyl, using known techniques. The esters of the general formula (11), wherein $R_d$ is $C_{1-4}$ alkyl and also acids of the general formula (11), wherein $R_d$ is H, may be prepared by reacting a compound of the general formula (2) with an ester or acid of the general formula (10a) in the presence of a suitable base, such as potassium carbonate or sodium hydride, in a suitable solvent, such as N,N-dimethylformamide. The esters or acids of the general formula (10a) are either commercially available or may be prepared by standard literature methods from commercially available materials.

Alternatively, as shown in Scheme 4, compounds of the general formula (11) may be prepared under Mitsunobu conditions by reacting a compound of the general formula (2) with a compound of the general formula (10b), wherein $R_d$ is $C_{1-4}$ alkyl, using a phosphine, such as triphenyl phosphine, and an azoester, such as diethyl azodicarboxylate.

Similarly, compounds of the general formula (1) may be prepared by reacting a compound of general formula (10d) with a compound of the general formula (2) under Mitsunobu conditions using a phosphine, such as triphenyl phosphine, and an azoester, such as diethyl azodicarboxylate. Compounds of general formula (10d) may be prepared from a compound of general formula (10c) and an amine of general formula (5) using suitable activating reagents such as 1-hydroxybenzotriazole and N-(3-dimethylamino-propyl)-N'-ethyl-carbodiimide hydrochloride. Compounds (10b) and (10c) are either known compounds or may be made from known compounds.

In another method, the compounds of the general formula (1) may be prepared by reacting an acid halide of the general formula (13) with an amine of the general formula (5) in a suitable solvent, such as dichloromethane, in the presence of a tertiary amine, such as triethylamine, and an activating agent, such as 4-dimethylaminopyridine.

As shown in Scheme 5, an acid halide of the general formula (13) may be prepared by chlorinating a compound of the general formula (12) with a suitable chlorinating agent, such as oxalyl chloride, in a suitable solvent, such as dichloro-methane, and in the presence of, for example, N,N-dimethylformamide. The compounds of the general formula (12) correspond to the compounds of general formula (11), wherein $R_d$ is H.

Scheme 5

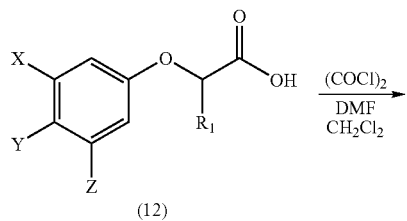

(12)

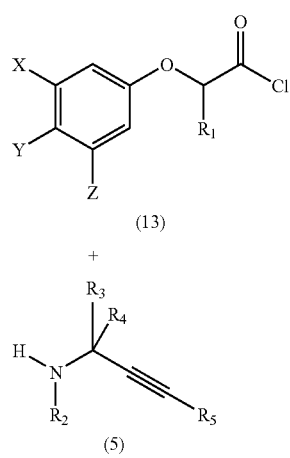

(1)

As shown in Scheme 6, compounds of the general formula (1), wherein $R_5$ is H, may be reacted under Sonogashira conditions with, for example, optionally substituted phenyl or thienyl chlorides, bromides, iodides or triflates to form substituted phenyl or thienyl compounds of the general formula (1), wherein $R_5$ is an optionally substituted phenyl or thienyl group. A suitable palladium catalyst is tetrakis (triphenylphosphine)-palladium(0).

Scheme 6

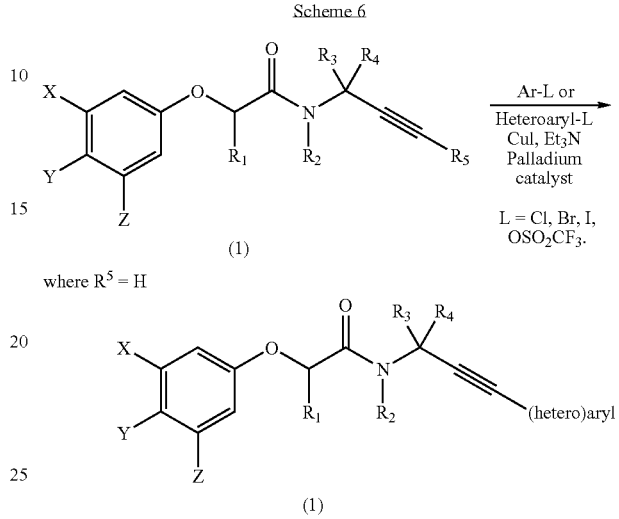

where $R^5$ = H

Compounds of the general formula (1) may be prepared as shown in Scheme 7. A phenoxyacetic acid of the general formula (14) may be treated with at least two equivalents of a strong base, such as lithium diisopropylamide, in a suitable solvent such as tetrahydrofuran, at a temperature between −78° C. and ambient temperature, with an alkylating agent $R_1L$ to give phenoxyalkylcarboxylic acids of the general formula (15) upon acidification.

Scheme 7

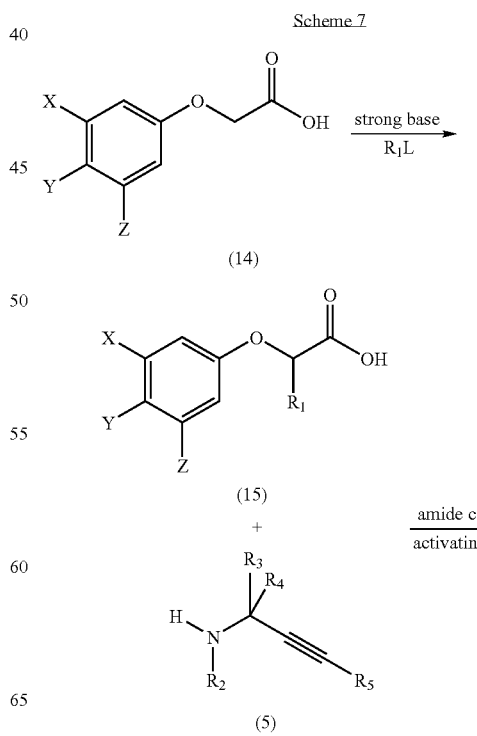

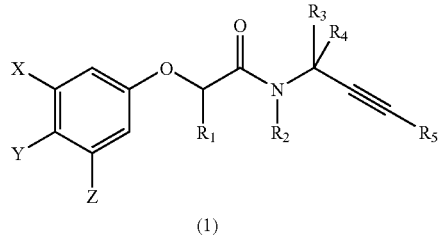

As shown in Scheme 8, compounds of general formula (1), where $R_5$ is for example 3-chloropropyl, can be reacted with various nucleophiles such as a metal cyanide salt, for example sodium cyanide, to give compounds of general formula (16), with metal alkoxides, for example sodium methoxide, to give compounds of general formula (17), with 1,2,4-triazole in the presence of base such as triethylamine to give compounds of general formula (18) and with metal thioalkoxides, for example sodium methanethiolate, to give compounds of general formula (19). Compounds of general formula (19) can be treated with oxidising agents such as sodium periodate, to give sulphoxides of general formula (20), or with oxidising agents such as 3-chloroperbenzoic acid, to give sulphones of general formula (21).

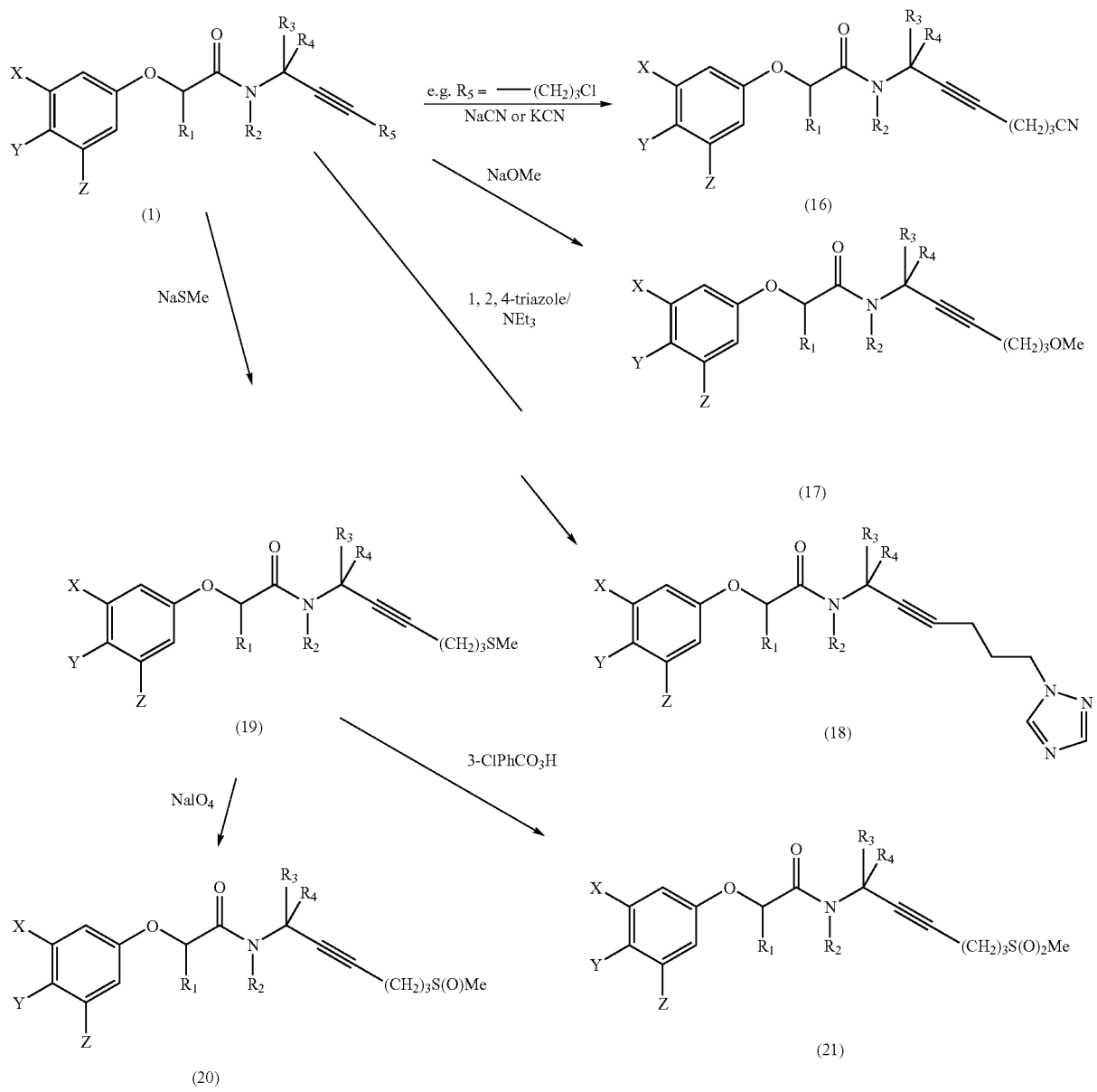

Other compounds of the invention may be prepared by transforming the substituents in the compounds of general formula (1) using known procedures e.g. by the alkylation of compounds of formula (1), wherein $R_2$ is H or $R_5$ is H.

The compounds of formula (1) are active fungicides and may be used to control one or more of the following pathogens: *Pyricularia oryzae* (*Magnaporthe grisea*) on rice and wheat and other *Pyriculria* spp. on other hosts; *Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillua taurica* on tomatoes, aubergine and green pepper, *Podosphaera leucotricha* on apples and *Uncinula necator* on vines; *Cochlobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colitotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoma piceae, Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (I) show particularly good activity against the Oomycete class of pathogens such as *Phytophthora infestans, Plasmopara* species, e.g. *Plasmopara viticola* and *Pythium* species e.g. *Pythium ultimum*.

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (1) either as a liquid (if it is not a liquid at room temperature, it may be melted at a reasonable temperature, typically below 70° C.) or in solution (by dissolving it in an appropriate solvent) and then emulsiflying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccina-mates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquino-late, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxycarbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrroInitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, teclofi-
alam, tecnazene, tetraconazole, thiabendazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

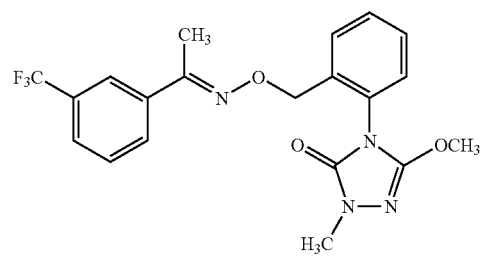

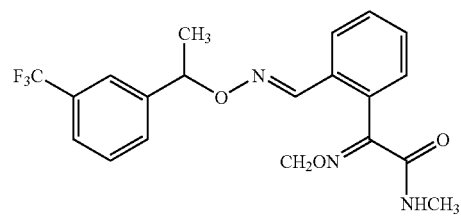

The compounds of formula (1) may be mixed with soil, peat or other rooting media for the protection of plants against seed-borne, soil-borne or foliar fungal diseases.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:

| | | | |
|---|---|---|---|
| ml = | millilitres | DMSO = | dimethylsulphoxide |
| g = | grammes | NMR = | nuclear magnetic resonance |
| ppm = | parts per million | HPLC = | high performance liquid chromatography |
| $M^+$ = | mass ion | | |
| s = | singlet | q = | quartet |
| d = | doublet | m = | multiplet |
| br s = | broad singlet | ppm = | parts per million |
| t = | triplet | | |

EXAMPLE 1

This Example illustrates the preparation of 2-(3,5-dichlorophenoxy)-3-methoxy-N-(4-methylpent-2-yn-4-yl)propionamide (Compound No. 4 in Table 1)

Stage 1: Preparation of methyl 2-bromo-3-methoxypropionate

Methyl 2,3-dibromopropionate (21.9 g) and trimethylamine N-oxide (0.1 g) in methanol (8 ml) were cooled to −5° C. with stirring under an atmosphere of nitrogen. A methanolic solution of sodium methoxide, freshly prepared from sodium (2.25 g) and methanol (24 ml), was added dropwise over 15 minutes to the mixture, which was maintained below 0° C. by cooling. On completion of addition, the mixture was stirred for a further 30 minutes and acetic acid (1 ml) was added followed by diethyl ether (100 ml). The mixture was filtered to remove insoluble salts and the filtrate evaporated under reduced pressure to give an oil, which was re-dissolved in a small volume of diethyl ether and re-filtered. The filtrate was evaporated under reduced pressure to give the required product (17.4 g) as a pale yellow oil.

$^1$H NMR (CDCl$_3$) δ: 3.41(3H, s); 3.74(1H, dd); 3.82(3H, s); 3.92(1H, dd); 4.34(1H, dd).

Stage 2: Preparation of methyl 2-(3,5-dichlorophenoxy)-3-methoxynropionate.

A solution of 3,5-dichlorophenol (0.815 g) in dry N,N-dimethylformamide (10 ml) was treated with anhydrous potassium carbonate (0.69 g) and methyl 2-bromo-3-methoxy-propionate (1.0 g) and stirred at 80° C. for 2 hours. The mixture was cooled to ambient temperature, made acidic with aqueous hydrochloric acid (2M) then extracted with diethyl ether. The organic extract was washed with water then brine, dried over magnesium sulphate, and evaporated under reduced pressure to give the required product (1.29 g) as a colourless oil.

Stage 3: Preparation of 2-(3,5-dichlorophenoxy)-3-methoxypropionic acid.

An emulsion of methyl 2-(3,5-dichlorophenyl)-3-methoxypropionate in sodium hydroxide (0.14 g) and water (2 ml) was stirred at ambient temperature for 2 hours when a clear solution was produced. The mixture was acidified with concentrated sulphuric acid (0.34 g), diluted with water then extracted with diethyl ether. The organic phase was separated, extracted with aqueous sodium hydrogen carbonate and the organic phase discarded. The basic aqueous extract was acidified with concentrated hydrochloric acid and extracted with diethyl ether. The extract was dried over magnesium sulphate and evaporated under reduced pressure to give a colourless oil, 0.50 g, containing a mixture of the required product and 2-(3,5-dichlorophenoxy)-acrylic acid in the ratio 2:1, which was used in the next Stage without further purification. 2-(3,5-Dichlorophenoxy)-3-methoxypropionic acid was characterised from its NMR spectrum.

$^1$H NMR (CDCl$_3$) δ: 3.48(3H, s); 3.92(2H, m); 4.82(1H, m); 6.84(2H, m); 7.02(1H, m); 8.05(1H, br s).

Stage 4

The product from Stage 3 (0.44 g) was dissolved in dry dichloromethane (10 ml) with stirring and oxalyl chloride (0.212 g) was added. When no further gas was evolved the mixture was evaporated under reduced pressure to give a pale yellow oil which contained 2-(3,5-dichlorophenyl)-3-methoxypropionic acid chloride. The acid chloride was dissolved in dry dichloromethane (5 ml) and 4-amino-4-methylpent-2-yne hydrochloride (prepared as described below; 0.222 g) was added. The suspension was stirred at ambient temperature whilst triethylamine (0.48 ml) was added dropwise. The mixture was stirred for 3 hours, diluted with water, acidified with dilute aqueous hydrochloric acid (2M) then extracted with further dichloromethane. The organic extract was separated, washed with brine then dried over magnesium sulphate and evaporated under reduced pressure to give a gum. The gum was fractionated by chromatography (silica; hexane:ethyl acetate, 3:1 by volume) to give the required product as a colourless solid, 0.28 g, mp 107-110° C.

$^1$H NMR (CDCl$_3$) δ: 1.59-1.61(6H, s); 1.80(3H, s); 3.40 (3H, s); 3.82(2H, m); 4.56(1H, m); 6.42(1H, s); 6.89(2H, m); 7.05(1H, m).

The 4-amino-4-methylpent-2-yne hydrochloride used above was prepared as follows.

Step 1

3-Amino-3-methylbutyne (commercially available as 90% aqueous solution; 16.6 g) was dissolved in dichloromethane (150 ml), dried over sodium sulphate and filtered to give a solution containing 14.9 g of amine. To the stirred solution of amine under an atmosphere of nitrogen at ambient temperature was added dry triethylamine (48.4 ml). 1,2-Bis-(chlorodimethylsilyl)ethane (38.98 g) in dichloromethane (100 ml) was then added dropwise, maintaining the reaction temperature at 15° C. by cooling. The mixture was stirred for 3 hours, the colourless solid, which had formed during the reaction, was filtered from solution and the filtrate was evaporated under reduced pressure to give a paste. The paste was extracted into hexane and refiltered. The filtrate was evaporated under reduced pressure and the oil obtained was distilled to give 1-(1,1-dimethyl-2-propynyl)-2,2,5,5-tetramethyl-1-aza-2,5-disilacyclopentane, 21.5 g, b.p. 41° C. at 0.06 mm Hg pressure.

$^1$H NMR (CDCl$_3$) δ: 0.16(12H, s); 0.60(4H, s); 1.48(6H, s); 2.24(1H, s).

Step 2

The product from Step 1 (13.0 g) in dry tetrahydrofuran (140 ml) was cooled to −70° C. under an atmosphere of nitrogen with stirring and a solution of n-butyl lithium (23.1 ml of 2.5M solution in hexanes) was added at −65 to −70° C. during 5 minutes. The mixture was allowed to warm to −5° C. and methyl iodide (3.93 ml) was added dropwise over 10 minutes. The reaction mixture was allowed to warm to 10° C. when an exothermic reaction occurred. The mixture was maintained at 20° C. by cooling for 2 hours then evaporated under reduced pressure to a small volume. The residue was dissolved in hexane, filtered to remove the insoluble material and evaporated under reduced pressure to give 1-(1,1-dimethyl-2-butynyl)-2,2,5,5-tetramethyl-1-aza-2,5-disilacyclopentane as a yellow oil, 13.0 g.

$^1$H NMR (CDCl$_3$) δ: 0.10(12H, s); 0.56(4H, s); 1.40(6H, s); 1.72(3H, s).

Step 3

The product from Step 2 (13.0 g) was added slowly to aqueous hydrochloric acid (35 ml, 4M) at 0° C. with stirring. The emulsion formed was stirred for 0.5 hours then taken to pH14 with aqueous sodium hydroxide (4M) while maintaining the reaction mixture at 0° C. by cooling in ice. The aqueous mixture was extracted into dichloromethane (three times) and the extracts combined, dried over sodium sulphate and filtered. The filtrate was made acidic by adding an excess of a saturated solution of hydrogen chloride in 1,4-dioxan. The mixture was concentrated under reduced pressure until a colourless precipitate was formed. Hexane was added to the suspension and the solid was filtered from solution. The solid was washed with dry diethyl ether and placed under vacuum to remove any residual solvents to give the required product as a colourless solid, 5.0 g.

$^1$H NMR (d$_6$-DMSO) δ: 1.74(6H, s); 1.82(3H, s); 8.74 (3H, br s).

EXAMPLE 2

The preparation of 2-(3,5-dichlorophenoxy)-3-methoxy-N-(3-methylbut-1-yn-3-yl)-propionamide (Compound No. 4 in Table 6)

2-(3,5-Dichlorophenoxy)-3-methoxy-N-(3-methylbut-1-yn-3-yl)propionamide was prepared in a similar way to 2-(3,5-dichlorophenoxy)-3-methoxy-N-(4-methylpent-2-yn-4-yl)propionamide as described in Example 1 except that 3-amino-3-methylbut-1-yne (commercially available as 90% aqueous solution) was used in place of 4-amino-4-methyl pent-2-yne in Stage 4.

EXAMPLE 3

This Example illustrates the preparation of 2-(3-cyano-5-methoxyphenoxy)-N-(2-methylpent-3-yn-2-yl)-3-methoxypropionamide (Compound No. 16 in Table 1)

Stage 1: Preparation of 2-bromo-N-(4-methylpent-2-yn-4-yl) 3-methoxypropionamide.

Step 1: Preparation of 2-bromo-3-methoxypropionic acid.

Methyl 2-bromo-3-methoxypropionate (1.00 g) in tetrahydrofuran (8 ml) was stirred at 10° C. and lithium hydroxide monohydrate (0.21 g) in water (1.5 ml) was added dropwise. On complete addition, the mixture was stirred for 1.5 hours. The colourless solution was evaporated under reduced pressure to a small volume and the aqueous solution was taken to pH 3 with dilute sulphuric acid. The mixture was extracted with diethyl ether (50 ml) and the organic phase separated, washed with brine, dried over magnesium sulphate then evaporated under reduced pressure to give the required product (0.6 g) as a colourless liquid.

$^1$H NMR (CDCl$_3$) δ: 3.45(3H, s); 3.78(1H, m); 3.92(1H, m); 4.38(1H, m); 6.65(1H, br s).

Step 2: Preparation of 2-bromo-N-(4-methylpent-2-yn-4-yl) 3-methoxypropionamide.

2-Bromo-3-methoxypropionic acid (0.366 g) was dissolved in dry dichloro-methane (4 ml) containing dry N,N-dimethylformamide (0.05 ml) with stirring and oxalyl chloride (0.254 g) was added. The mixture was stirred at ambient temperature for 2 hours then evaporated under reduced pressure to give 2-bromo-3-methoxypropionic acid chloride (C=O, ν 1780 cms$^{-1}$). The acid chloride was dissolved in dry dichloromethane (6 ml) and 4-amino-4-methylpent-2-yne hydrochloride (0.267 g) was added. The mixture was cooled to 3° C. and triethylamine (0.404 g) was added dropwise, while keeping the reaction temperature between 0-5° C. The suspension that had formed was stirred at ambient temperature for 1 hour, diluted with further dichloromethane and washed with hydrochloric acid (2M). The organic phase was separated, dried over magnesium sulfate and evaporated under reduced pressure to give a gum. The gum was fractionated by chromatography (silica: hexane/ethyl acetate, 3:2 by volume) to give the required product (0.300 g) as a colourless solid. $^1$H NMR (CDCl$_3$) δ: 1.63 (6H, s); 1.82(3H, s); 3.44(3H, s); 3.88(2H, m); 4.32(1H, m); 6.62(1H, s).

Stage 2

3-Cyano-5-methoxyphenol (prepared as described in *J. Med. Chem.* (1993), 36, No 16, 2367; 0.119 g) in dry N,N-dimethylformamide (3 ml) containing anhydrous potassium carbonate (0.168 g) and 2-bromo-N-(4-methylpent-2-yn-4-yl) 3-methoxypropionamide (0.210 g) were stirred and heated to 80° C. for 5 hours. The mixture was cooled to ambient temperature, stored for 2 days then poured into water and extracted with ethyl acetate. The organic phases were combined, washed with water, dried over magnesium sulphate then evaporated under reduced pressure to give a brown gum. The gum was fractionated by chromatography (silica; hexane/ethyl acetate 3:2 by volume) to give the required product (0.110 g) as a colourless gum.

$^1$H NMR (CDCl$_3$) δ: 1.60(3H, s); 1.62 (3H, s); 1.72(3H, s); 3.42(3H, s); 3.80-3.87(2H, m and 3H, s); 4.59(1H, m); 6.44(1H, s); 6.77(1H, m); 6.85(2H, m).

EXAMPLE 4

The preparation of 2-(3-chloro-5-methoxyphenoxy)-N-(2-methylpent-3-yn-2-yl)-3-methoxypropionamide (Compound No. 17 in Table 1)

2-(3-Chloro-5-methoxyphenoxy)-N-(2-methylpent-3-yn-2-yl)-3-methoxypropionamide, a colourless gum, was prepared in a similar manner to 2-(3-cyano-5-methoxyphenoxy)-N-(2-methylpent-3-yn-2-yl)-3-methoxypropionamide as described in Example 3 except that 3-chloro-5-methoxyphenol was used instead of 3-cyano-5-methoxyphenol.

$^1$H NMR (CDCl$_3$) δ: 1.58(3H, s); 1.60 (3H, s); 1.79(3H, s); 3.41(3H, s); 3.77(3H, s); 3.79-3.86(2H, m); 4.56(1H, m); 6.49(1H, s); 6.43(1H, m); 6.58(2H, m).

EXAMPLE 5

This Example illustrates the preparation of 2-(3,5-dichlorophenoxy)-N-(1-methoxy-4-methylpent-2-yn-4-yl)-3-methoxypropionamide (Compound No. 4 in Table 16)

Stage 1: Preparation of 2-bromo-N-(1-methoxy-4-methylpent-2-Yn-4-yl)-3-methoxy-propionamide Step 1: Preparation of 4-amino-1-methoxy-4-methylpent-2-yne hydrochloride 1-(1,1-Dimethyl-2-propynyl)-2,2,5,5-tetramethyl-1-aza-2,5-disilacyclopentane (22.6 g) in dry tetrahydrofuran (250 ml) was cooled to −50° C. under an atmosphere of nitrogen with stirring and a solution of n-butyl lithium (44 ml, 2.5M solution in hexanes) was added dropwise over 10 minutes. The mixture was stirred for 0.5 hour, allowed to warm to −20° C. and formaldehyde gas bubbled through the mixture until no starting material remained, as determined by glc analysis. On completion of the reaction, the mixture was treated with water, the ether phase separated, the aqueous phase extracted with ethyl acetate (twice) and the organic extracts combined and washed with water (three times). The combined organic extract was dried over magnesium sulphate and evaporated under reduced pressure to give 4-methyl-4-(2,2,5,5-tetramethyl-1-aza-2,5-disilacyclopent-1-yl)pent-2-yn-1-ol (24.96 g) as a pale yellow liquid.

$^1$H NMR (CDCl$_3$) δ: 0.00(12H, s); 0.46(4H, s); 1.32(6H, s); 4.10(2H, s).

4-Methyl-4-(2,2,5,5-tetramethyl-1-aza-2,5-disilacyclopent-1-yl)pent-2-yn-1-ol (2.55 g) in dry tetrahydrofuran (30 ml) was cooled to −10° C. under an atmosphere of nitrogen with stirring and potassium bis(trimethylsilyl)amide (2.09 g) in dry tetrahydrofuran (25 ml) was added over 5 minutes then the mixture was stirred at −(10 to 5)° C. for 0.75 hours. Methyl iodide (1.49 g) in tetrahydrofuran (10 ml) was added over 5 minutes and the mixture was allowed to warm to ambient temperature over 2 hour then stored for 18 hours. The mixture was diluted with water and extracted with ethyl acetate (three times). The extracts were combined, washed with water, dried over magnesium sulphate and evaporated under reduced pressure to give 1-(1-methoxy-4-methylpent-2-yn-4-yl)-2,2,5,5-tetramethyl-1-aza-2,5-disilacyclopentane as a yellow liquid. This liquid was stirred with dilute aqueous hydrochloric acid (30 ml) for 0.25 hours, washed with diethyl ether (twice) and the aqueous acidic phase separated then evaporated under reduced pressure. The residue was evaporated under reduced pressure with toluene (twice) to remove any water, dissolved in dichloromethane and dried over magnesium sulphate then evaporated under reduced pressure to give 4-amino-1-methoxy-4-methylpent-2-yne hydrochloride, 0.66 g, as a pale yellow solid.

$^1$H NMR (CDCl$_3$) δ: 1.78(6H, s); 3.40(3H, s); 4.12(2H, s); 8.88(3H, br s).

Step 2

2-Bromo-N-(1-methoxy-4-methylpent-2-yn-4-yl)-3-methoxypropionamide was prepared from 2-bromo-1-methoxypropionic acid in a similar manner to 2-bromo-N-(4-methylpent-2-yn-4-yl)-3-methoxypropionamide described in Example 3, Stage 1, Step 2 using 4-amino-1-methoxy-4-methylpent-2-yne hydrochloride in place of 4-amino-4-methylpent-2-yne hydrochloride.

$^1$H NMR (CDCl$_3$) δ: 1.68(6H, s); 3.38(3H, s), 3.44(3H, s); 3.82-3.92-(2H, m); 4.10(2H, s); 4.33(1H, t); 6.64(1H, br s), yellow gum.

Stage 2

3,5-Dichlorophenol (0.10 g), 2-bromo-N-(1-methoxy-4-methylpent-2-yn-4-yl)-3-methoxypropiona (0.18 g) and anhydrous potassium carbonate (0.10 g) were stirred in dry N,N-dimethylformamide (5 ml) at 80° C. for 2 hours then cooled to ambient temperature and stored for 18 hours. The mixture was diluted with water, extracted with ethyl acetate (three times) and the extracts were combined, washed with water, dried over magnesium sulphate and then evaporated under reduced pressure to leave an oil. The oil was fractionated by chromatography (silica; ethyl acetate) to give 2-(3,5-dichlorophenyl)-N-(1-methoxy-4-methylpent-2-yn-4-yl)-3-methoxypropionamide, 0.13 g, as a colourless oil.

$^1$H NMR (CDCl$_3$) δ: 1.66(3H, s); 1.68(3H, s); 3.38(3H, s); 3.42(3H, s); 3.78-3.86-(2H, m); 4.12(1H, t); 4.56-4.60 (1H, t); 6.44(1H, br s); 6.88(2H, s); 7.06(1H, s).

EXAMPLE 6

This Example illustrates the preparation of 2-(3,4,5-trimethylphenoxy)-3-methoxy-N-(4-methylpent-2-yn-4-yl)propionamide (Compound No. 3 in Table 1)

In a similar procedure to Example 3 Stage 2, 3,4,5-trimethylphenol was reacted with 2-bromo-N-(4-methylpent-2-yn-4-yl) 3-methoxypropionamide to give the title product as a colourless gum. $^1$H NMR (CDCl$_3$) δ: 1.61(6H, s); 1.80(3H, s); 2.11(3H, s); 2.26(6H, s); 3.40(3H, s); 3.82 (2H, m); 4.53(1H, t); 6.62(2H, s); 6.66(1H, s).

EXAMPLE 7

This Example illustrates the fungicidal properties of compounds of formula (1).

The compounds were tested in a leaf disk assay, with methods described below. The test compounds were dissolved in DMSO and diluted into water to 200 ppm. In the case of the test on *Pythium ultimum*, they were dissolved in DMSO and diluted into water to 20 ppm.

*Erysiphe graminis* f.sp. *hordei* (barley powdery mildew): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Erysiphe graminis* f.sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f.sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia oryzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Pythium ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added. The test plate was incubated at 24° C. and the inhibition of growth was determined photometrically after 48 hours.

The following Compounds [Compound No (Table)] gave at least 70% control of the following fungal infections at 200 ppm:

*Phytophthora infestans:* 3(1), 4(1), 4(6), 4(16)
*Plasmopara viticola:* 3(1), 4(1), 4(6), 4(16)
*Erysiphe graminis* f.sp. *hordei:* 4(1)

The following Compound gave at least 70% control of the following fungal infection at 20 ppm:

*Pythium ultimum:* 3(1), 4(1), 4(16).

What is claimed is:

1. A compound of the formula (1):

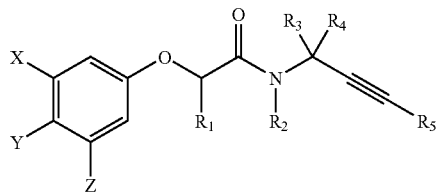

wherein
- X, Y and Z are independently H, halogen, $C_{1-4}$ alkyl, halo($C_{1-4}$)alkyl, $C_{2-4}$ alkenyl, halo($C_{2-4}$)alkenyl $C_{2-4}$ alkynyl, halo($C_{2-4}$)alkynyl, $C_{1-4}$ alkoxy, halo($C_{1-4}$) alkoxy, —S(O)$_n$($C_{1-4}$)alkyl where n is 0, 1 or 2 and the alkyl group is optionally substituted with fluoro, —OSO$_2$($C_{1-4}$)alkyl where the alkyl group is optionally substituted with fluoro, cyano, nitro, $C_{1-4}$ alkoxycarbonyl, —CONR'R", —COR', —NR'COR" or —NR'COOR''' where R' and R" are independently H or $C_{1-4}$ alkyl and R''' is $C_{1-4}$ alkyl, provided that at least one of X and Z is other than H;
- $R_1$ is alkoxyalkyl, alkylthioalkyl, alkylsulphinylalkyl or alkylsulphonylalkyl in which the total number of carbon atoms is 2 or 3;
- $R_2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy; $R_3$ and $R_4$ are independently H, $C_{1-3}$ alkyl, $C_{2-3}$ alkenyl or $C_{2-3}$ alkynyl provided that both are not H and that when both are other than H their combined total of carbon atoms does not exceed 4, or
- $R_3$ and $R_4$ join with the carbon atom to which they are attached to form a 3 or 4 membered carbocyclic ring optionally containing one O, S or N atom and optionally substituted with halo or $C_{1-4}$ alkyl; and
- $R_5$ is H, $C_{1-4}$ alkyl or $C_{3-6}$ cycloalkyl in which the alkyl or cycloalkyl group is optionally substituted with halo, hydroxy, $C_{1-6}$ alkoxy, cyano, $C_{1-4}$ alkylcarbonyloxy, aminocarbonyloxy, mono- or di($C_{1-4}$)alkylaminocarbonyloxy, —S(O)$_n$($C_{1-6}$)alkyl where n is 0, 1 or 2, triazolyl, tri($C_{1-4}$)alkylsilyloxy, optionally substituted phenoxy, optionally substituted thienyloxy, optionally substituted benzyloxy or optionally substituted thienylmethoxy, or
- $R_5$ is optionally substituted phenyl, optionally substituted thienyl or optionally substituted benzyl, in which the optionally substituted phenyl and thienyl rings of the $R_5$ values are optionally substituted with one, two or three substituents selected from halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$) alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$cycloalkyl, $C_{3-6}$ cycloalkyl($C_{1-4}$)alkyl, phenoxy, benzyloxy, benzoyloxy, cyano, isocyano, thiocyanato, isothiocyanato, nitro, —NR'''R", —NHCOR''', —NHCONR'''R", —CONR'''R", —SO$_2$R''', —OSO$_2$R''', —COR''', —CR'''=NR" or —N=CR'''R", in which R''' and R" are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

2. A compound according to claim 1 wherein X, Y and Z are all chloro or methyl, or X and Z are both chloro or bromo and Y is H or methyl, or X and Z are both methyl or methoxy and Y is H, chloro, bromo or alkylthio, or X is methoxy, Y is H and Z is cyano or chloro, or X is methyl, Y is H and Z is ethyl, or X is chloro, bromo or trifluoromethyl and both Y and Z are H.

3. A compound according to claim 1 wherein $R_1$ is methoxymethyl, methylthiomethyl, ethoxymethyl, 2-methoxyethyl, 2-methylthioethyl.

4. A compound according to claim 1 wherein $R_1$ is methoxymethyl.

5. A compound according to claim 1 wherein $R_2$ is H.

6. A compound according to claim 1 wherein both $R_3$ and $R_4$ are methyl.

7. A compound according to claim 1 wherein $R_5$ is H, methyl, hydroxymethyl, methoxymethyl, 1-methoxyethyl, tert-butyldimethylsiloxymethyl, 3-cyanopropyl, 3-methoxypropyl, 3-(1,2,4-triazol-1-yl)propyl, 3-methylthiopropyl, 3-methanesulphinylpropyl or 3-methanesulphonylpropyl.

8. A compound according to claim 1 wherein
X, Y and Z are independently H, halogen, $C_{1-4}$ alkyl, halo($C_{1-4}$)alkyl, $C_{2-4}$ alkenyl, halo($C_{2-4}$)alkenyl, $C_{2-4}$ alkynyl, halo($C_{2-4}$)alkynyl, $C_{1-4}$ alkoxy, halo($C_{1-4}$) alkoxy, —S(O)$_n$($C_{1-4}$)alkyl where n is 0, 1 or 2 and the alkyl group is optionally substituted with fluoro, —OSO$_2$($C_{1-4}$)alkyl where the alkyl group is optionally substituted with fluoro, cyano, nitro, $C_{1-4}$ alkoxycarbonyl, —CONR'R", —COR' or —NR'COR" where R' and R″ are independently H or $C_{1-4}$ alkyl, provided that at least one of X and Z is other than H;

$R_1$ is alkoxyalkyl, alkylthioalkyl, alkylsulphinylalkyl or alkylsulphonylalkyl in which the total number of carbon atoms is 2 or 3;

$R_2$ is H, $C_{1-4}$ alkyl, $C_{1-4}$ alkoxymethyl or benzyloxymethyl in which the phenyl ring of the benzyl moiety is optionally substituted with $C_{1-4}$ alkoxy;

$R_3$ and $R_4$ are independently H, $C_{1-3}$ alkyl, $C_{2-3}$ alkenyl or $C_{2-3}$ alkynyl provided that both are not H and that when both are other than H their combined total of carbon atoms does not exceed 4, or $R_3$ and $R_4$ join with the carbon atom to which they are attached to form a 3 or 4 membered carbocyclic ring optionally containing one O, S or N atom and optionally substituted with halo or $C_{1-4}$ alkyl; and $R_5$ is H, $C_{1-4}$ alkyl or $C_{3-6}$ cycloalkyl in which the alkyl or cycloalkyl group is optionally substituted with halo, hydroxy, $C_{1-6}$ alkoxy, $C_{1-6}$ alkylthio, cyano, $C_{1-4}$ alkylcarbonyloxy, aminocarbonyloxy or mono- or di($C_{1-4}$) alkylaminocarbonyloxy, tri($C_{1-4}$)alkylsilyloxy, optionally substituted phenoxy, optionally substituted thienyloxy, optionally substituted benzyloxy or optionally substituted thienylmethoxy, or $R_5$ is optionally substituted phenyl, optionally substituted thienyl or optionally substituted benzyl, in which the optionally substituted phenyl and thienyl rings of the $R_5$ values are optionally substituted with one, two or three substituents selected from halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$) alkyl, halo($C_{1-4}$)alkoxy, $C_{1-4}$ alkylthio, halo($C_{1-4}$)alkylthio, hydroxy($C_{1-4}$)alkyl, $C_{1-4}$alkoxy($C_{1-4}$)alkyl, $C_{3-6}$ cycloalkyl, $C_{3-6}$ cyclo-alkyl($C_{1-4}$)alkyl, phenoxy, benzyloxy, benzoyloxy, cyano, isocyano, thiocyanato, isothiocyanato, nitro, —NR‴R″, —NHCOR‴, —NHCONR‴R″, —CONR‴R″, —SO$_2$R‴, —OSO$_2$R‴, —COR‴, —CR‴=NR″ or —N=CR‴R″, in which R‴ and R″ are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

9. A compound according to claim 1 wherein X, Y and Z are all chloro or methyl, or X and Z are both chloro or bromo and Y is H or methyl, or X and Z are both methyl or methoxy and Y is H, chloro, bromo or alkylthio, or X is methoxy, Y is H and Z is cyano or chloro, or X is methyl, Y is H and Z is ethyl, or X is chloro, bromo or trifluoromethyl and both Y and Z are H; $R_1$ is methoxymethyl, methylthiomethyl, ethoxymethyl, 2-methoxyethyl or 2-methylthioethyl; $R_2$ is H; $R_3$ and $R_4$ are both methyl; and $R_5$ is H, methyl, hydroxymethyl, methoxymethyl, 1-methoxyethyl, tert-butyldimethylsiloxymethyl, 3-cyanopropyl, 3-methoxypropyl, 3-(1,2,4-triazol-1-yl)propyl, 3-methyl-thiopropyl, 3-methanesulphinylpropyl or 3-methanesulphonylpropyl.

10. A fungicidal composition comprising a fungicidally effective amount of a compound of the formula (1) according to claim 1 and a suitable carrier or diluent therefor.

11. A method of combating or controlling phytopathogenic fungi which comprises applying a fungicidally effective amount of a compound of the formula (1) according to claim 1 to a plant, to a seed of a plant, to the locus of the plant or seed or to soil or to plant growth medium.

* * * * *